(12) United States Patent
Cho et al.

(10) Patent No.: US 12,116,590 B2
(45) Date of Patent: Oct. 15, 2024

(54) METHOD FOR MASS-PRODUCING PLANT EXOSOMES

(71) Applicants: Industry-University Cooperation Foundation Hanyang University ERICA Campus, Ansan (KR); EXOSTEMTECH CO., LTD., Ansan (KR)

(72) Inventors: Yong-Woo Cho, Seongnam (KR); Ji-Suk Choi, Gunpo (KR); Young-Chan Choi, Chuncheon (KR); Min-Kang Kim, Namyangju (KR)

(73) Assignees: Industry-University Cooperation Foundation Hanyang University ERICA Campus, Ansan (KR); EXOSTEMTECH CO., LTD., Gyeonggi-do (KR)

( * ) Notice: Subject to any disclaimer, the term of this patent is extended or adjusted under 35 U.S.C. 154(b) by 275 days.

(21) Appl. No.: 17/623,857

(22) PCT Filed: Apr. 10, 2020

(86) PCT No.: PCT/KR2020/004906
§ 371 (c)(1),
(2) Date: Dec. 29, 2021

(87) PCT Pub. No.: WO2021/002571
PCT Pub. Date: Jan. 7, 2021

(65) Prior Publication Data
US 2022/0364051 A1 Nov. 17, 2022

(30) Foreign Application Priority Data
Jul. 2, 2019 (KR) ......................... 10-2019-0079490

(51) Int. Cl.
*C12N 15/82* (2006.01)
*B01D 61/14* (2006.01)
*B01D 61/16* (2006.01)
*C12N 5/04* (2006.01)

(52) U.S. Cl.
CPC ............. *C12N 5/04* (2013.01); *B01D 61/145* (2013.01); *B01D 61/16* (2013.01); *B01D 2311/2676* (2013.01)

(58) Field of Classification Search
None
See application file for complete search history.

(56) References Cited

U.S. PATENT DOCUMENTS

| | | | |
|---|---|---|---|
| 2012/0202268 A1 | 8/2012 | De Vocht et al. | |
| 2017/0296626 A1* | 10/2017 | Tarnopolsky | A61K 9/5176 |
| 2018/0256488 A1* | 9/2018 | Choi | A61K 8/9789 |
| 2018/0263871 A1 | 9/2018 | Choi | |
| 2018/0271773 A1 | 9/2018 | Lee et al. | |
| 2020/0121723 A1 | 4/2020 | Yi | |
| 2021/0283183 A1 | 9/2021 | Cho | |

FOREIGN PATENT DOCUMENTS

| | | | |
|---|---|---|---|
| CN | 106083863 A | | 11/2016 |
| JP | 2018-528971 A | | 10/2018 |
| JP | 2018-530546 A | | 10/2018 |
| KR | 10-2012-0093957 A | | 8/2012 |
| KR | 10-2017-003780 A | * | 4/2017 |
| KR | 10-2017-0037380 A | * | 4/2017 |
| KR | 10-1895916 B1 | * | 9/2018 |
| KR | 10-18959160000 B1 | * | 9/2018 |
| KR | 10-2019-0050286 A | | 5/2019 |
| KR | 10-2019-0052644 A | | 5/2019 |
| WO | WO-2017-052267 | * | 3/2017 |
| WO | 2017/203260 A1 | | 11/2017 |
| WO | 2018/026203 A1 | | 2/2018 |
| WO | 2018/062973 A1 | | 4/2018 |
| WO | 2019/004738 A2 | | 1/2019 |
| WO | 2019/035057 A2 | | 2/2019 |
| WO | 2019/035880 A1 | | 2/2019 |
| WO | 2019/060719 A1 | | 3/2019 |
| WO | 2020/041782 A1 | | 2/2020 |

OTHER PUBLICATIONS

Lee et al. (English Translation of WO 2017/052267 A1, Published, Published Mar. 3, 2017).*
The Extended European Search Report for European Patent Application No. 20835489.4, dated Jun. 20, 2023.

* cited by examiner

*Primary Examiner* — Vinod Kumar

(57) ABSTRACT

The present disclosure relates to a large-scale production method of plant exosomes. The method of the present disclosure can isolate high purity plant exosomes from a large amount of raw plants, using centrifugation and TFF, which can process a large amount of plant raw materials at once. This improves a conventional isolation process of plant exosomes stayed at the laboratory level, and thereby, suggests an easy process for large-scale production.

7 Claims, 5 Drawing Sheets

METHOD FOR MASS-PRODUCING PLANT EXOSOMES

TECHNICAL FIELD

The present application claims the priority based on Korean Application No. 10-2019-0079490 filed on Jul. 2, 2019, and all contents disclosed in the description and drawings of the corresponding application are incorporated herein by reference.

The present disclosure relates to a method for isolating exosomes from a raw plant, including a plant having hard flesh or peel. More specifically, the present disclosure relates to a method for large-scale production of high purity plant exosomes from a raw plant so as to be usefully used in related industries such as pharmaceuticals and commercialized products, and the like.

BACKGROUND ART

It has been reported that exosomes are nano-sized microvesicles secreted from various cells and contain proteins, lipids, mRNA and miRNA, and act as an important mediator of intercellular communication by acting on the endocrine system. This role is attracting attention as a new therapeutic agent that can overcome problems of conventional stem cell therapeutic agents such as engraftment rate and immunogenicity.

According to a recent study, exosomes separated from edible plants have no toxicity or immunogenicity compared to exosomes secreted from mammalian cells, and are known to have very high in vivo stability and biocompatibility. In addition, it was reported that exosomes separated from mammalian cells contain about 20% cholesterol, but edible plant exosomes do not contain cholesterol. In particular, compared to animal tissue or cell culture solution, raw plants have the advantage that it can be obtained in a large amount.

Various plants are included in the exosomes according to derived plants, but until now, little is known about proteins related to plant exosomes, and there is a limitation in confirming characteristics compared to the exosomes of mammalian cells. In most studies, the characteristics of plant exosomes are confirmed by the size or shape of exosomes, and in order to isolate plant exosomes, a method for selecting an appropriate size and isolating only exosomes is needed.

In case of the prior art, an attempt has been made to isolate plant exosomes through a density gradient ultracentrifugation method using a sucrose gradient, but this method is difficult to utilize in the production process for commercialization of exosomes. In addition, there is a method to obtain a material with a size smaller than pores of a filtration filter by filtering separated extracellular vesicles, which is that when isolating exosomes from a large amount of plant juices, as impurities or exosomes are adsorbed and accumulated in the filter pores, the filtration efficiency is rapidly lowered, which is very disadvantageous for long-term exosome isolation.

Numerous documents are referenced throughout the present description, and citations thereof are indicated. The disclosures of the cited documents are incorporated herein by reference in their entirety to more clearly explain the level of the art to which the present disclosure pertains and the content of the present disclosure.

Technical Problem

In the present disclosure, a large-scale production process using centrifugation and TFF is suggested as a method for isolating high purity plant exosomes. Through the present disclosure, the purification and productivity of the high purity plant exosomes were effectively improved.

Accordingly, an object of the present disclosure provides a method capable of effectively isolating high purity plant exosomes on a large scale, complementing the conventional isolation methods.

Another object of the present disclosure is to provide a method for isolating high purity exosomes on a large scale with uniform particle size and distribution from a raw plant.

Other object of the present disclosure is to provide a method for isolating plant exosomes without limitation of the raw plant, including a marine plant group such as hard peel, stem, seed and sea mustard, laver, and the like, different from the methods limited to soft flesh or juices in the prior art.

Other object of the present disclosure is to provide a method for isolation of plant derived exosomes that is suitable for GMP production of medical and commercial products, and facilitates process scale-up.

Other object and benefit of the present disclosure will become more apparent from the following detailed description of the invention, claims and drawings.

Technical Solution

One aspect of the present disclosure is to provide a method for isolating plant exosomes, comprising performing centrifugation; and performing tangential-flow filtration (TFF) as ultrafiltration.

The term used herein, "plant exosomes" refers to exosomes or exosome-like extracellular vesicles having a size of about 50~200 nm isolated from plants.

Plant derived exosomes are known to have low toxicity and immunogenicity compared to exosomes secreted from mammalian cells, and have very low cholesterol content, so their stability and biocompatibility are very high. In addition, plant derived exosomes are known to be effective in wound healing and skin regeneration due to plant-derived antioxidant components or protein components.

In the meantime, as various methods for separating exosomes from living organisms, centrifugation, ultracentrifugation, density gradient centrifugation, chromatography, filtration, ultrafiltration, tangential-flow filtration, polymer-based precipitation, total exosome extraction kit and immunoaffinity separation method, and the like have been developed. However, in case of this prior art, the exosome isolation method is limited to a method for isolating exosomes from an animal, limitedly, a mammal-derived cell or a biological solution (such as milk). Since vacuoles similar to exosomes are found in plant derived cells, unlike animal derived cells, methods for removing them have been introduced, but most are limited to laboratory-level doses.

In the present disclosure, by particularly combining ultracentrifugation and tangential-flow filtration as ultrafiltration among conventionally known exosome isolation methods, a method for isolation of plant derived exosomes which can prevent contamination by impurities such as vacuoles and deterioration of purity, and obtain high purity plant exosomes on a large scale is provided. It is difficult to obtain plant exosomes from which vacuoles are removed by any other combination of two methods among previously known exosome separation methods, other than the combination, and in particular, it is impossible to uniformly obtain high purity plant exosomes on a large scale.

Plant derived exosomes may have uniform size distribution of 30 to 500 nm, and preferably, it may have uniform size distribution of 50 to 200 nm.

In another aspect, to substitute for the conventional density gradient centrifugation method limited to small production of plant exosomes, a large-scale production method of plant exosomes using centrifugation and TFF method is provided.

The centrifugation used in the present disclosure is a separation method using a density difference between a solid and a liquid surrounding the solid, and refers to a method for accelerating sedimentation of the solid using centrifugal force. Centrifugation has advantages of being able to repeat the process continuously, process a large amount in a short time, and allow easy operation in a sterile state. The centrifugation of the present disclosure may be differential centrifugation, density gradient centrifugation or a combination thereof, but not limited thereto.

The centrifugation method used in the present disclosure may be selected from low-speed centrifugation, high-speed centrifugation, ultracentrifugation and a combination thereof, and preferably, it may include ultracentrifugation. Low-speed centrifugation can achieve a speed of 6,000 rpm (6,000×g) or less, and is mainly used for centrifugation of samples that precipitate easily such as cells or nuclei, and high-speed centrifugation has a maximum speed of about 20,000-25,000 rpm (60,000×g), and ultracentrifugation refers to a centrifugation method with a maximum speed of about 40,000-80,000 rpm (600,000×g).

Previously, ultracentrifugation was known to have a low yield and damage exosomes during the separation process, so it could not be used for mass isolation of exosomes, and only laboratory-level separation was possible. However, the present inventors surprisingly found that plant exosomes, unlike animal exosomes, can effectively improve productivity without exosome damage through ultracentrifugation, and can be applied to the exosome mass production process. In one embodiment, the centrifugation of the present disclosure may be performed by comprising (a) a process of obtaining a supernatant after centrifugation for 10 to 30 minutes under a centrifugation condition at a speed of 1,000 to 3,000×g, (b) a process of removing vacuoles by ultracentrifugation for 60 minutes to 2 hours under a ultracentrifugation condition at a speed of 10,000 to 50,000×g, and (c) a process of obtaining pellets comprising exosomes by ultracentrifugation for 60 minutes to 2 hours under a ultracentrifugation condition at a speed of 100,000 to 150,000×g.

In addition, the method of the present disclosure is characterized in that it comprises performing tangential-flow filtration (TFF). Tangential-flow filtration (TFF) used in the present disclosure is a filtration method in which a solution flows in a direction perpendicular to the filtration membrane, filters out small-sized impurities present in the solution, and separates large-sized exosomes. It is possible to minimize adsorption of exosomes to pores of the filtration filter or clogging of the membrane pores compared to the conventional filtration methods, and thus it is easy to process scale-up and GMP process application.

In TFF, the rapid flow of the feed solution acts to reduce the concentration polarization (product concentration on the pore surface) while 'sweeping' the membrane or hollow fiber surface. In addition, the TFF method prevents an increase of contaminants that can clog the pores. This rapid cross flow drops the pressure, which can force some of the feed solution and dissolved molecules smaller than the pores of the membrane or hollow fiber to pass through the filter. The solution that has passed through the pores is called a filtrate or a permeate, and molecules or particles larger than the pores remain in the feed solution and are effectively concentrated. In a preferable embodiment, the TFF of the present disclosure is an ultrafiltration system, and as the result of performing the TFF method as described above, the centrifuged extract can be efficiently concentrated to a volume of 1/10 to 1/100. Ultrafiltration, which is located in the middle of microfiltration and reverse osmosis, is a method of separating specific substances by the size difference between membrane pores and solutes. The ultrafiltration membrane can exhibit its separation performance as a molecular weight cutoff (MWCO) defined as the minimum molecular weight of a solute that exhibits 90% or more exclusion by the membrane.

The tangential-flow filtration used in the present disclosure may be one or more selected from the group consisting of hollow fiber TFF and membrane TFF capable of performing ultrafiltration, and preferably, it may use a TFF filter with a molecular weight cutoff (MWCO) of 100,000 Da to 500,000 Da.

Furthermore, the method of the present disclosure may further comprise crushing a raw plant before the centrifugation and TFF. In this case, there is an advantage in that the range of the raw plant, which was limited to soft flesh, can be expanded to hard plants including peel, and the like, through a mechanical and physical crushing. Therefore, the raw plant used in the method of the present disclosure may comprise one or more selected from the group consisting of flesh, peel, seed, stem, leaves, roots and flowers.

The crushing a raw plant may include a process of mechanically crushing a mixture in which a raw plant and a buffer solution are mixed in a range of a weight ratio of 1:1 to 1:10, and as the buffer solution, one comprising one or more of phosphate-buffered saline (PBS), tris-buffered saline (TBS), 4-(2-hydroxyethyl)-1-piperazineethanesulfonic acid(HEPES)-buffered saline (HBS) physiological saline solution, distilled water, culture medium, water for injection, and the like may be used, but not limited thereto.

The process of crushing a raw plant may be performed by mechanically crushing a plant mixture with a blade of a knife rotating at a speed of 10 to 1,000 rpm.

The extract obtained by this method of the present disclosure may comprise plant exosomes at a concentration of the number of particles of $10^7$ to $10^{12}$ per unit volume of 1 mL.

The method of the present disclosure as described above has an advantage in that it is suitable for large-scale production of plant exosomes, and large-scale processing of raw plant 1 mL or more, 10 mL or more, 100 mL or more, 1 L or more, 10 L or more or 100 L or more per time is possible.

Effects

The method of the present disclosure provides a method for uniformly obtaining high purity exosomes from which vacuoles are removed. In particular, using centrifugation and TFF, which can process a large amount of plant raw materials at once, high purity plant exosomes can be isolated from a large amount of a raw plant. This improves a conventional isolation process of plant exosomes stayed at the laboratory level, and thereby, suggests an easy process for large-scale production.

MODE FOR INVENTION

Hereinafter, the present disclosure will be described in more detail through examples. These examples are only for illustrating the present disclosure more specifically, and it will be apparent to those skilled in the art to which the present disclosure pertains that the scope of the present disclosure is not limited by these examples.

EXAMPLE

1. Aloe Peel Derived Exosomes
(1) Isolation Method
Example 1 (UC+TFF)

Aloe peel derived exosomes were isolated using UC and TFF. Specifically, aloe peel was sufficiently grinded after putting in a mixer setting to 1:2 (w/w) with phosphate-buffered saline (PBS). Then, supernatant generated after centrifugation at 1,000×g for 10 minutes was centrifuged at 2000×g for 20 minutes, and then the supernatant was collected again. The supernatant was centrifuged at 3,000×g for 30 minutes and then centrifuged at 10,000×g for 60 minutes. The supernatant after 10,000×g was ultracentrifuged at 100,000×g for 70 minutes at 4° C. using UC.

The remaining pellets after UC were suspended and exosomes were isolated from the suspension through a tangential-flow filtration (TFF) system. Specifically, other impurity particles smaller than the pores of the filter were removed from the surface of the multi-filter having a cutoff value of 100 to 500 kDa, and the solution containing aloe peel derived exosomes was concentrated. The exosomes isolated in this way were stored frozen at −70° C. or less until used in the experiment.

Comparative Example 1 (MF+TFF)

Aloe peel derived exosomes were isolated using microfiltration and TFF. Specifically, the aloe peel was sufficiently grinded after putting in a mixer setting to 1:2 (w/w) with phosphate-buffered saline (PBS). Then, to obtain exosomes with high purity in which the particle size distribution is uniform, 2% by weight of trehalose was added. After adding trehalose, this was filtered with a 0.22 μm filter, and impurities such as cell debris, wastes and large particles were removed.

After passing through the filtering process, through a tangential-flow filtration (TFF) system as ultrafiltration, exosomes were isolated. Specifically, other impurity particles smaller than the pores of the filter were removed from the surface of the multi-filter having a cutoff value of 100 to 500 kDa, and the solution containing aloe peel derived exosomes was concentrated. The exosomes isolated in this way were stored frozen at −70° C. or less until used in the experiment.

(2) Evaluation of Characteristics of Exosomes

For aloe peel derived exosomes, evaluation of exosome characteristics was progressed. In order to confirm the shape of exosomes, a scanning electron microscope (TEM) was used, and in order to confirm the accurate microparticle size, a dynamic light scattering photometer (DLS) was used. The particle number of the isolated exosomes per unit volume was confirmed through nanoparticle tracking analysis (NTA).

Figure 1:
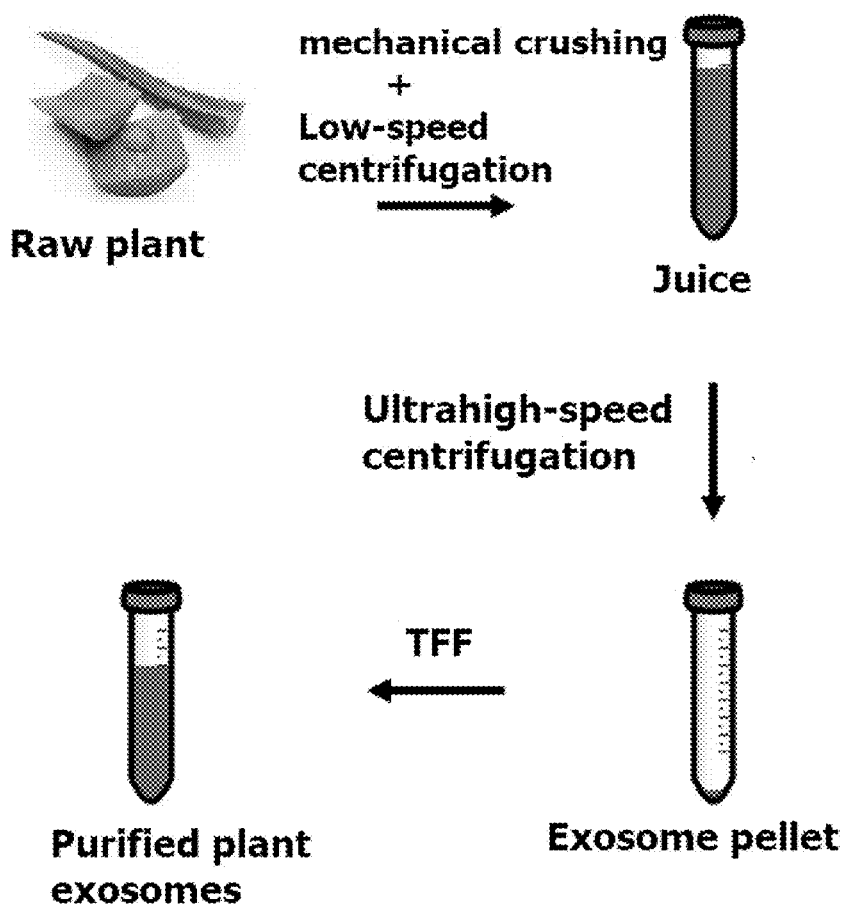
FIG. 1 is a schematic diagram of a process for a method of isolation of plant derived exosomes according to one embodiment of the present disclosure.
Figure 2:
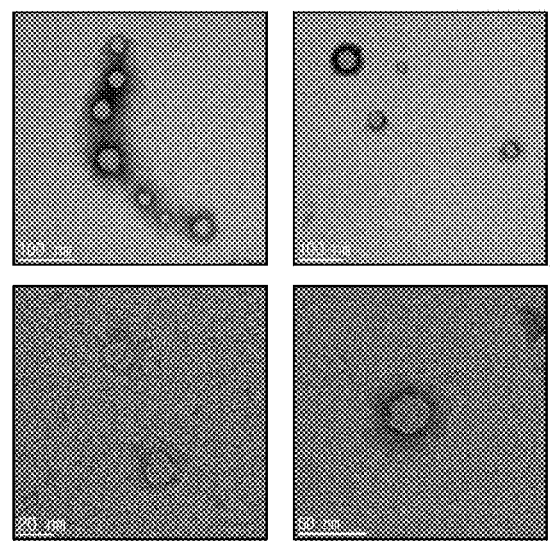
FIG. 2 is the result of form analysis (TEM) of aloe peel derived exosomes according to Example 1.
Figure 3:
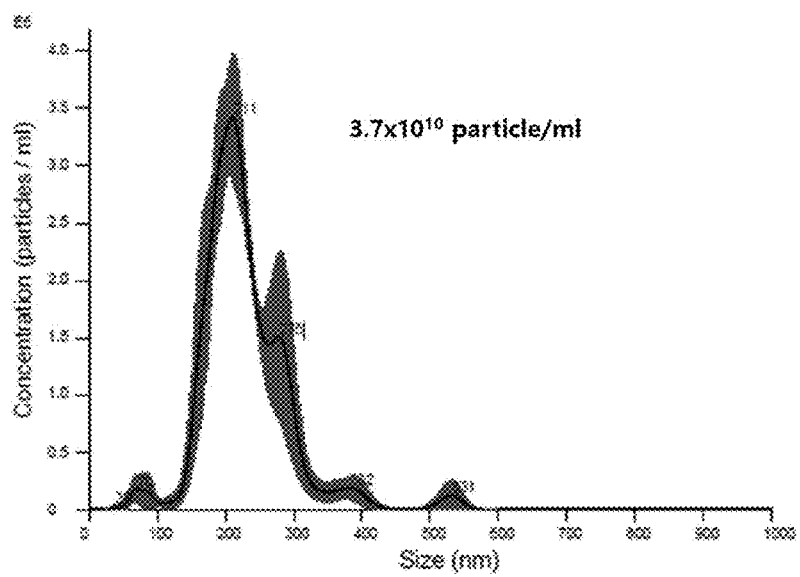
FIG. 3 is the result of characteristic analysis (NTA) of aloe peel derived exosomes according to Example 1.

As a result of the experiment, in Example 1, a mixture in which exosomes and vacuoles were present together was obtained after filtering solids with a relatively large particle size by microfiltration (pore size 0.1~1.0 μm) of the supernatant after 10,000×g centrifugation, and it was confirmed that exosomes and vacuoles were mixed in the supernatant after 10,000×g centrifugation. In Example 1, it was confirmed that a large amount of impurities such as proteins and nucleic acids as well as exosomes were mixed in the pellet collected after performing 100,000×g ultracentrifugation. As a result of isolating exosomes by performing ultrafiltration, TFF in Example 1, $1\times10^{9\sim11}$ high purity exosomes per unit volume of 1 mL were isolated. It was confirmed that the isolated aloe peel derived exosomes had a microstructure of 200 nm or less (FIG. 2), and the concentration of $1\times10^{9\sim11}$ exosomes per unit volume of 1 mL was confirmed through nanoparticle tracking analysis (NTA) (FIG. 3).

Figure 4:
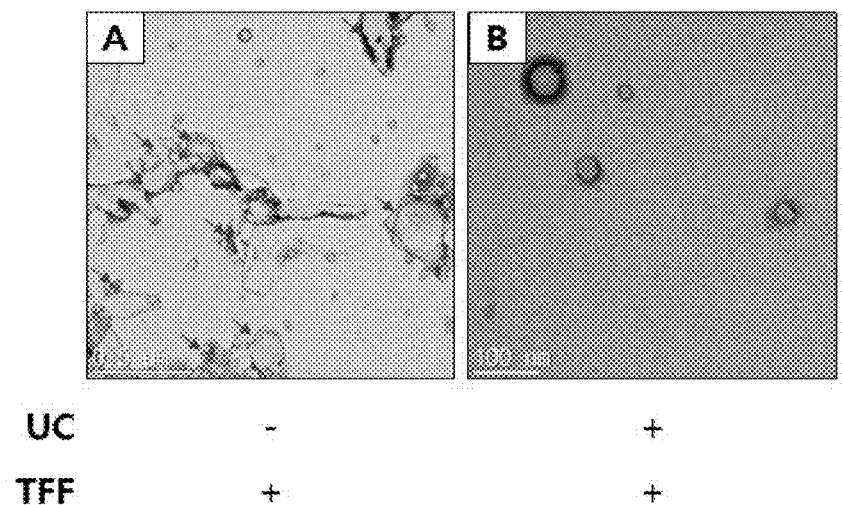
FIG. 4 is a TEM photograph of comparing the results obtained when omitting the UC process and performing only TFF and the results obtained when combining UC and TFF.
Figure 5:
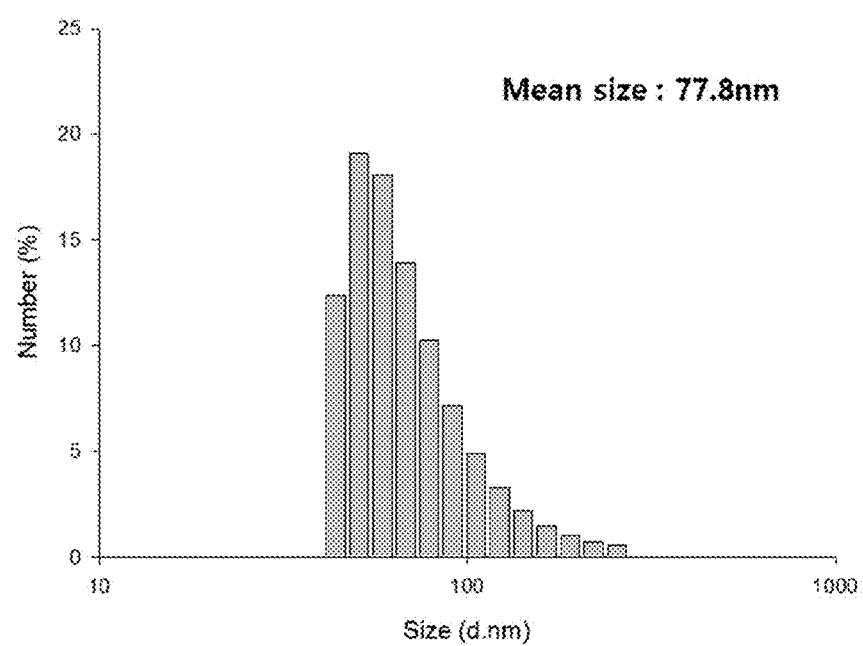
FIG. 5 is the result of characteristic analysis (DLS) of aloe peel derived exosomes according to Example 1.

On the other hand, it was observed that vacuoles similar to exosomes were mixed in the aloe peel derived extract isolated by the method of Comparative example 1, and thereby, it was confirmed that it was difficult to remove vacuoles contained in the plant extract by the MF and TFF methods. In other words, when performing TFF only without an ultracentrifugation (UC) process in the process of isolating exosomes from aloe peel, it was clearly confirmed that impurities including vacuoles (red arrow) were included in addition to exosomes, and these impurities cause a decrease in the efficacy of plant exosomes (See FIG. 4).

2. Isolation of Garlic Derived Exosomes
(1) Isolation Method
Example 2 (UC+TFF):

Garlic derived exosomes were isolated using UC and TFF. Specifically, garlic from which peel was removed was sufficiently grinded after putting in a mixer setting to 1:2 (w/w) with phosphate-buffered saline (PBS). Then, supernatant generated after centrifugation at 1,000×g for 10 minutes was centrifuged at 2000×g for 20 minutes, and then the supernatant was collected again. The supernatant was centrifuged at 3,000×g for 30 minutes and then centrifuged at 10,000×g for 60 minutes. The supernatant after 10,000×g was ultracentrifuged at 100,000×g for 70 minutes at 4° C. using UC. By suspending the pellet remained after UC, exosomes were isolated through a tangential-flow filtration (TFF) system as ultrafiltration. Specifically, other impurity particles smaller than the pores of the filter were removed from the surface of the multi-filter having a cutoff value of 100 to 500 kDa, and the solution containing garlic derived exosomes was concentrated. The exosomes isolated in this way were stored frozen at −70° C. or less until used in the experiment.

Comparative Example 2 (UC+S-DGUC)

Garlic derived exosomes were isolated using UC and Sucrose-Density Gradient Ultracentrifugation. Specifically, garlic from which peel was removed was sufficiently grinded after putting in a mixer setting to 1:2 (w/w) with phosphate-buffered saline (PBS). Then, supernatant generated after centrifugation at 1,000×g for 10 minutes was centrifuged at 2000×g for 20 minutes, and then the supernatant was collected again. The supernatant was centrifuged at 3,000×g for 30 minutes and then centrifuged at 10,000×g for 60 minutes. The supernatant after 10,000×g was ultracentrifuged at 100,000×g for 70 minutes at 4° C. using UC.

By suspending the pellet remained after UC, Sucrose-Density Gradient Ultracentrifugation was additionally performed. Specifically, a sucrose solution having a density gradient was added in a centrifugation tube for ultracentrifugation. These sucrose solutions were made into 90%, 80%, 70%, 60%, 50%, 40% and 30% solutions, respectively, and after sterilization at 124° C. for 15 minutes, the tube for ultracentrifugation was carefully placed to have a layer of 90%~30%. After carefully adding the suspension containing the exosomes to the top of the sucrose gradient tube for ultracentrifugation prepared as above, using a centrifuge for ultracentrifugation, ultracentrifugation at 4° C., 200,000×g for 4 hours was performed. Then, fractions were obtained by 1 ml from the top of the tube, and the density was measured to obtain fractions corresponding to exosomes and washed to separate sucrose.

(2) Evaluation of Characteristics of Exosomes

Figure 6:
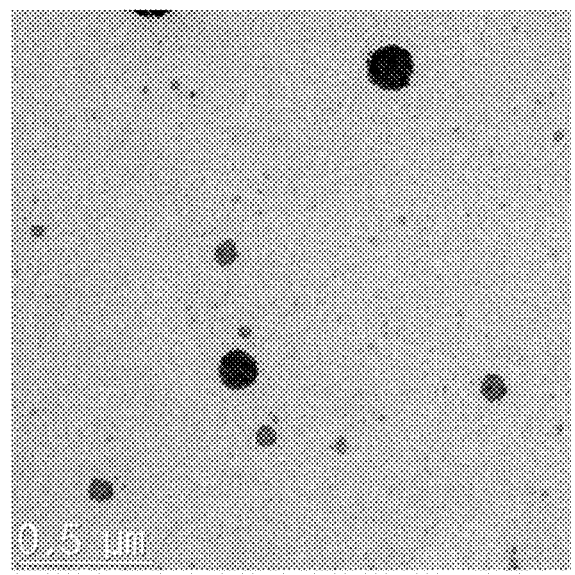
FIG. 6 is the result of form analysis (TEM) of garlic derived exosomes according to Example 2.
Figure 7:
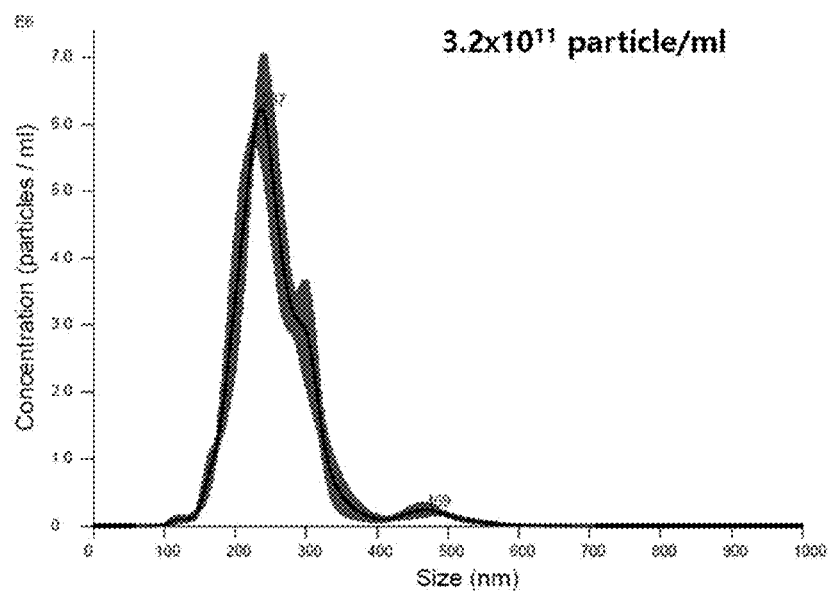
FIG. 7 is the result of characteristic analysis (NTA) of garlic derived exosomes according to Example 2.

As an experimental result, it was confirmed that the garlic derived exosomes isolated in Example 2 had a round microstructure of 200 nm or less through a scanning electron microscope (TEM) (FIG. 6), and as the result of confirming the particle number per unit volume of the isolated exosomes through nanoparticle tracking analysis (NTA), the concentration of $1\times10^{10\sim12}$ exosomes per unit volume of 1 mL was confirmed (FIG. 7).

It was observed that the garlic derived exosomes isolated by the method of Comparative example 2 also had a round microstructure of 200 nm or less through a scanning electron microscope (TEM). However, in order to isolate high purity exosomes, an additional washing process for separating sucrose was required, and the exosome production per hour was less than 1/100 of the production of Example 2. Therefore, it was confirmed that the method of Comparative example 2 was difficult to utilize in a mass production process for commercialization of exosomes.

3. Isolation of Sea Mustard Derived Exosomes
(1) Isolation Method
Example 3 (UC+TFF):

Sea mustard derived exosomes were isolated using UC and TFF. Specifically, sea mustard from which moisture was removed was sufficiently grinded after putting in a mixer setting to 1:2 (w/w) with phosphate-buffered saline (PBS). Then, supernatant generated after centrifugation at 1,000×g for 10 minutes was centrifuged at 2000×g for 20 minutes, and then the supernatant was collected again. The supernatant was centrifuged at 3,000×g for 30 minutes and then centrifuged at 10,000×g for 60 minutes. The supernatant after 10,000×g was ultracentrifuged at 100,000×g for 70 minutes at 4° C. using UC.

By suspending the pellet remained after UC, exosomes were isolated through a tangential-flow filtration (TFF) system as ultrafiltration. Specifically, other impurity particles smaller than the pores of the filter were removed from the surface of the multi-filter having a cutoff value of 100 to 500 kDa in the TFF system, and the solution containing sea mustard derived exosomes was concentrated. The exosomes isolated in this way were stored frozen at −70° C. or less until used in the experiment.

Comparative Example 3 (SEC+TFF):

Size Exclusion Chromatography was known as a useful method capable of separating exosomes without exosome damage or change in characteristics. Accordingly, sea mustard derived exosomes were isolated using SEC and TFF. Specifically, separation of exosomes by SEC was performed by the method disclosed in Boing et al (Single-step isolation of extracellular vesicles by size-exclusion chromatography, J Extracell Vesicles, 2014:1-11). 12 mL of Sepharose CL-2B (Sigma Aldrich, St. Louis, MO, USA) was stacked in a 20 mL syringe (BD Plasticpakc™, San Jose, CA), washed with PBS and equilibrated. 2 mL of sample was loaded onto a column, and fractions were collected using PBS as an elution buffer.

Exosomes were isolated from the collected fractions through a tangential-flow filtration (TFF) system. Specifically, other impurity particles smaller than the pores of the filter were removed from the surface of the multi-filter having a cutoff value of 100 to 500 kDa in the TFF system, and the solution containing sea mustard derived exosomes was concentrated. The exosomes isolated in this way were stored frozen at −70° C. or less until used in the experiment.

(2) Evaluation of Characteristics of Exosomes

Figure 8:
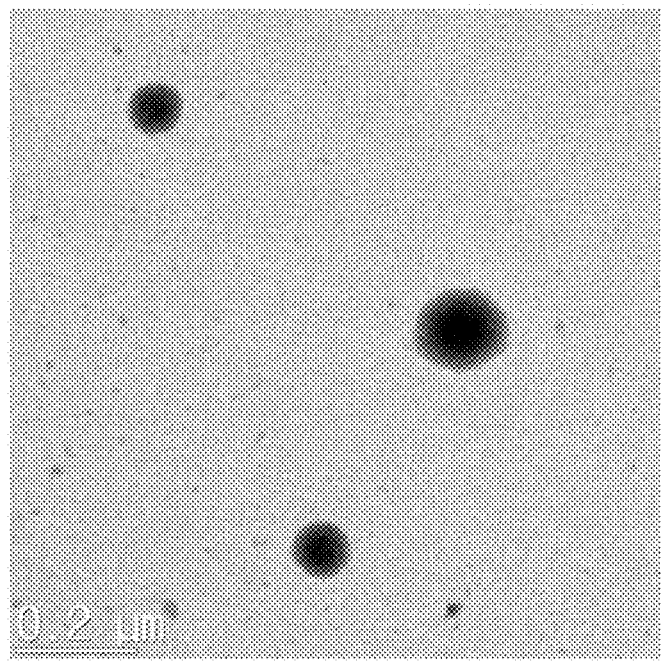
FIG. 8 is the result of form analysis (TEM) of sea mustard peel derived exosomes according to Example 3.
Figure 9:
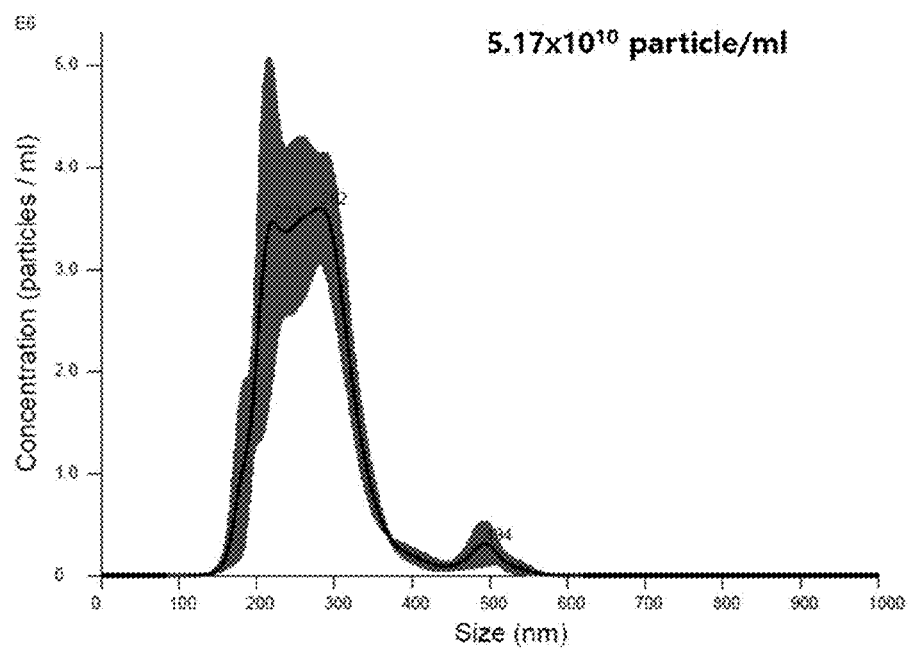
FIG. 9 is the result of form analysis (NTA) of sea mustard peel derived exosomes according to Example 3.

It was confirmed that the sea mustard derived exosomes isolated in Example 3 had a round microstructure of 200 nm or less through a scanning electron microscope (TEM) (FIG. 8), and as the result of confirming the particle number per unit volume of the isolated exosomes through nanoparticle tracking analysis (NTA), the concentration of $1\times10^{9\sim11}$ exosomes per unit volume of 1 mL was confirmed (FIG. 9).

On the other hand, it was observed that vacuoles similar to exosomes were mixed in the sea mustard derived extract isolated by the method of Comparative example 3, and therefore, it was confirmed that it was difficult to remove vacuoles contained in the plant extract by the SEC and TFF methods.

The invention claimed is:

1. A method for preparing a high-purity plant exosome extract, the method comprising:
    preparing a plant extract from a raw plant material;
    performing centrifugation of the plant extract at 10,000 to 50,000×g, and obtaining a supernatant;
    performing ultracentrifugation at 100,000 to 600,000×g using the supernatant, and obtaining a pellet;
    suspending the pellet to obtain a suspension;
    performing tangential-flow filtration (TFF) using the suspension; and
    obtaining the high-purity plant exosome extract, wherein the high-purity plant exosome extract comprises plant exosomes at a concentration of $10^7$ to $10^{12}$ particles per 1 ml of the high purity plant exosome extract, and wherein the high purity plant exosome extract lacks vacuoles.

2. The method for preparing a high-purity plant exosome extract according to claim 1, wherein the tangential-flow filtration is one or more selected from the group consisting of hollow fiber TFF and membrane TFF.

3. The method for preparing a high-purity plant exosome extract according to claim 1, wherein the tangential-flow filtration uses a TFF filter with a molecular weight cutoff (MWCO) of 100,000 Da to 500,000 Da.

4. The method for preparing a high-purity plant exosome extract according to claim 1, wherein the raw plant material comprises one or more selected from the group consisting of pulps, peels, seeds, stems, leaves, roots and flowers.

5. The method for preparing a high-purity plant exosome extract according to claim 1, wherein said plant exosomes have a diameter of 50 to 200 nm.

6. The method for preparing a high-purity plant exosome extract according to claim 1, wherein the high-purity plant exosome extract comprises said plant exosomes at a concentration of $1 \times 10^{9-11}$ particles per 1 ml of the plant extract.

7. The method for preparing a high-purity plant exosome extract according to claim 1, wherein the method is for a large-scale production of plant-derived exosomes, wherein the large-scale production comprises producing plant-derived exosomes by processing more than 1 mL of the extract prepared from the raw plant material per hour.

\* \* \* \* \*